United States Patent
Govari et al.

(10) Patent No.: US 9,480,416 B2
(45) Date of Patent: Nov. 1, 2016

(54) SIGNAL TRANSMISSION USING CATHETER BRAID WIRES

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 112 days.

(21) Appl. No.: 14/157,739

(22) Filed: Jan. 17, 2014

(65) Prior Publication Data

US 2015/0201864 A1  Jul. 23, 2015

(51) Int. Cl.
| | |
|---|---|
| A61B 5/05 | (2006.01) |
| A61B 5/06 | (2006.01) |
| A61M 25/00 | (2006.01) |
| A61B 5/02 | (2006.01) |
| A61B 5/00 | (2006.01) |
| A61M 25/01 | (2006.01) |

(52) U.S. Cl.
CPC ........... *A61B 5/062* (2013.01); *A61B 5/02028* (2013.01); *A61B 5/6851* (2013.01); *A61B 5/6852* (2013.01); *A61B 5/7203* (2013.01); *A61B 34/20* (2016.02); *A61M 25/0012* (2013.01); *A61M 25/0127* (2013.01); *A61B 2034/2051* (2016.02); *A61B 2562/0223* (2013.01); *A61B 2562/12* (2013.01); *A61M 25/005* (2013.01); *Y10T 29/49117* (2015.01)

(58) Field of Classification Search
USPC ..................................................... 600/409
See application file for complete search history.

(56) References Cited

U.S. PATENT DOCUMENTS

| | | |
|---|---|---|
| 5,391,199 A | 2/1995 | Ben-Haim |
| 6,171,240 B1 | 1/2001 | Young |
| 6,213,995 B1 | 4/2001 | Steen et al. |
| 6,239,724 B1 | 5/2001 | Doron |
| 6,332,089 B1 | 12/2001 | Acker |
| 6,484,118 B1 | 11/2002 | Govari |
| 6,618,612 B1 | 9/2003 | Acker |
| 6,690,963 B2 | 2/2004 | Ben-Haim |
| 7,881,769 B2 | 2/2011 | Sobe |
| 2002/0065455 A1 | 5/2002 | Ben-Haim |
| 2002/0151807 A1* | 10/2002 | Goldin .................. 600/509 |
| 2003/0120150 A1 | 6/2003 | Govari |
| 2004/0068178 A1 | 4/2004 | Govari |
| 2009/0192412 A1* | 7/2009 | Sela et al. .................. 600/585 |
| 2011/0066029 A1 | 3/2011 | Lyu et al. |
| 2011/0156700 A1 | 6/2011 | Kariv |
| 2012/0172842 A1* | 7/2012 | Sela et al. .................. 604/528 |
| 2012/0182014 A1 | 7/2012 | Rivera |

FOREIGN PATENT DOCUMENTS

WO   WO 96/05768 A1   2/1996

OTHER PUBLICATIONS

European Search Report dated Jun. 12, 2015 for corresponding Application No. EP15151379.

* cited by examiner

*Primary Examiner* — Joel F Brutus

(57) ABSTRACT

A probe includes an insertion tube, a magnetic field sensor, a dummy load mounted adjacent to the magnetic field sensor, and a braid. The braid includes multiple braid wires that traverse a length of the insertion tube. A first pair of the braid wires is connected across the magnetic field sensor, and a second pair of the braid wires is connected across the dummy load.

18 Claims, 3 Drawing Sheets

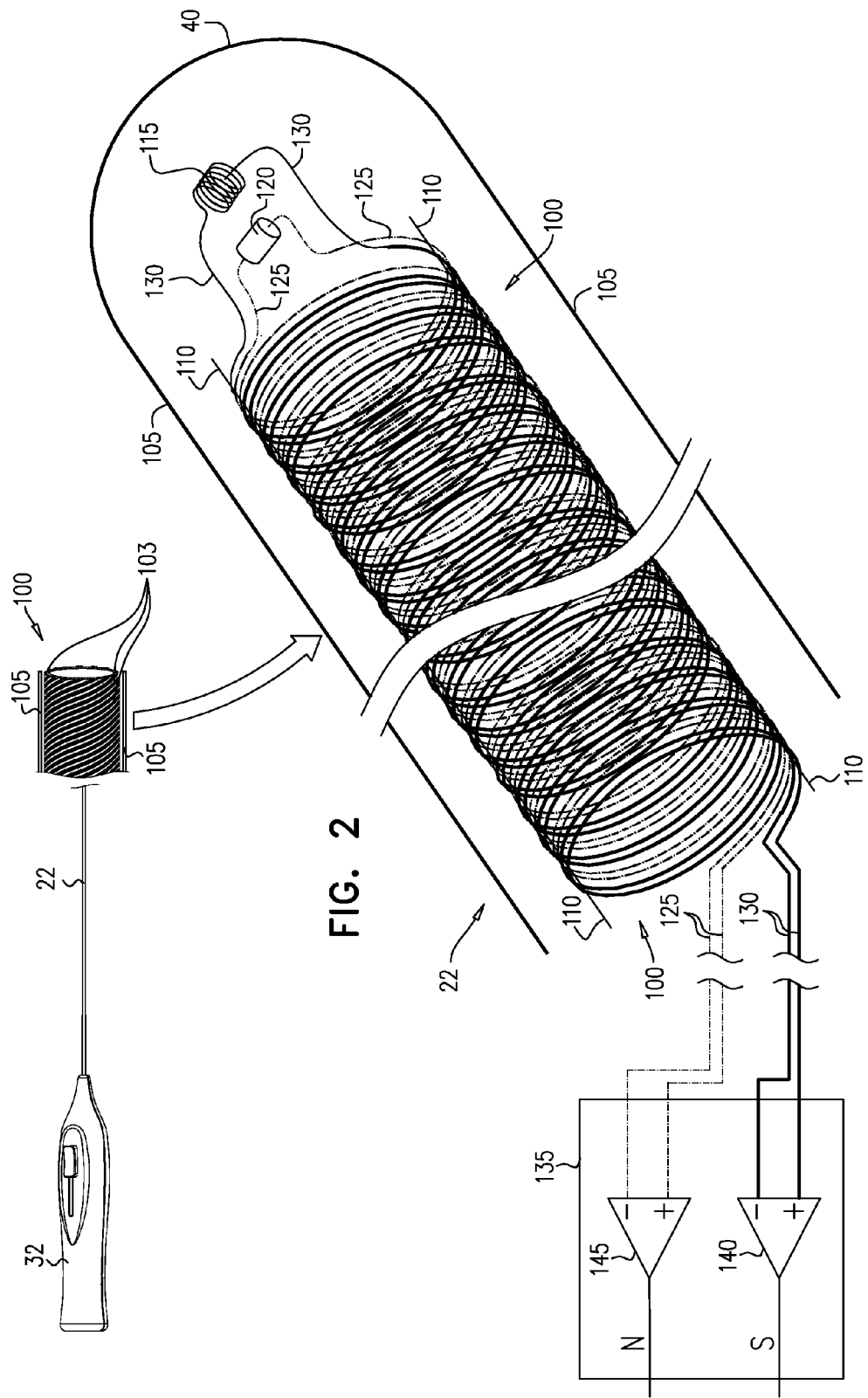

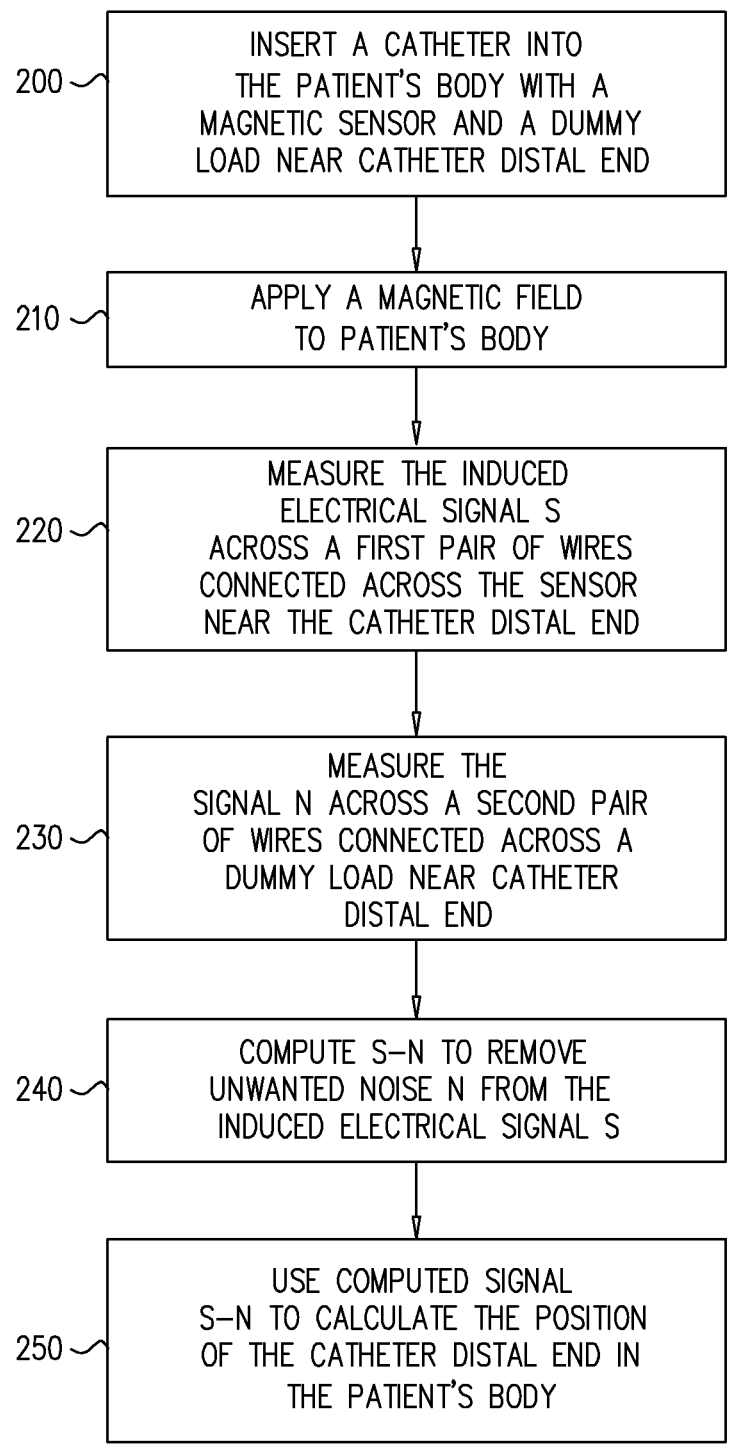

SIGNAL TRANSMISSION USING CATHETER BRAID WIRES

FIELD OF THE INVENTION

The present invention relates generally to intra-body probes, and particularly to methods and systems for transmitting electrical signals in intra-body probes.

BACKGROUND OF THE INVENTION

Magnetic field detectors installed near the distal end of catheters are used in medical positioning systems to identify the position of the catheter distal end in the body of a patient. The catheter distal end sensor is typically connected to the medical positioning system via cabling traversing the catheter lumen.

U.S. Pat. No. 7,881,769, whose disclosure is incorporated herein by reference, describes a catheter for performing a medical operation on an organic lumen, the catheter including an elongated member, a medical operational element located at a distal end of the elongated member, an electromagnetic field detector located at the distal end, and a wiring for coupling the electromagnetic field detector with a medical positioning system, wherein the medical positioning system determines the position and orientation of the distal end.

U.S. Patent Application Number US 2012/0182014, whose disclosure is incorporated herein by reference, describes a magnetic resonance imaging device, which includes an elongate flexible member having a proximal end, a distal end, and a lumen extending between the proximal end and the distal end and a solenoid coil affixed to the distal end of the elongate flexible member, the solenoid coil having a plurality of wire turns, the solenoid coil connected to a twisted-pair of leads extending proximally along the length of the flexible member. A connector is disposed at the proximal end of the elongate flexible member, the connector operatively coupled to the twisted-pair of leads. In an alternative embodiment, a coaxial cable substitutes for the lumen-containing elongate flexible member.

SUMMARY OF THE INVENTION

An embodiment of the present invention provides a probe including an insertion tube, a magnetic field sensor, a dummy load mounted adjacent to the magnetic field sensor, and a braid. The braid includes multiple braid wires that traverse a length of the insertion tube. A first pair of the braid wires is connected across the magnetic field sensor, and a second pair of the braid wires is connected across the dummy load.

In some embodiments the magnetic sensor includes a single-axis sensor. In other embodiments, the probe includes a cardiac catheter. In yet other embodiments, the probe includes a cardiac guide-wire. In other embodiments, each of the braid wires in the first and second pairs is electrically-insulated from the other braid wires.

In some embodiments, the probe includes an elongate flexible member that is contained within the insertion tube, such that the braid is located between the insertion tube and the elongate flexible member. In other embodiments, the probe includes circuitry that is configured to cancel interference in a first signal transferred over the first pair using a second signal transferred over the second pair. In yet other embodiments, the circuitry is configured to subtract the second signal from the first signal.

There is also provided, in accordance with an embodiment of the present invention, a method for fabricating a probe, including mounting a magnetic field sensor and a dummy load adjacent to one another in an insertion tube. A braid is placed along the insertion tube, the braid including multiple braid wires so as to traverse a length of the insertion tube. A first pair of the braid wires is connected across the magnetic field sensor, and a second pair of the braid wires is connected across the dummy load.

There is also provided, in accordance with an embodiment of the present invention, a method for position tracking, including inserting into a living body a probe, which includes an insertion tube, a magnetic field sensor, a dummy load mounted adjacent to the magnetic field sensor, and a braid including multiple braid wires that traverse a length of the insertion tube. A first pair of the braid wires is connected across the magnetic field sensor, and a second pair of the braid wires is connected across the dummy load. A magnetic field is applied to the living body. A first signal is measured across the first pair. A second signal is measured across the second pair. The second signal is applied to the first signal so as to remove interference from the first signal. A position of the magnetic field sensor in the living body is computed from the first signal after removing the interference.

In some embodiments, applying the second signal to the first signal includes subtracting the second signal from the first signal.

There is also provided, in accordance with an embodiment of the present invention, a position tracking system including a probe and an external subsystem. The probe is inserted into a living body and includes an insertion tube, a magnetic field sensor, a dummy load mounted adjacent to the magnetic field sensor, and a braid including multiple braid wires that traverse a length of the insertion tube. A first pair of the braid wires is connected across the magnetic field sensor, and a second pair of the braid wires is connected across the dummy load. The external subsystem is configured to apply a magnetic field to the living body, to measure a first signal across the first pair, to measure a second signal across the second pair, to apply the second signal to the first signal so as to remove interference from the first signal, and to compute a position of the magnetic field sensor in the living body from the first signal after removing the interference.

The present invention will be more fully understood from the following detailed description of the embodiments thereof, taken together with the drawings in which:

BRIEF DESCRIPTION OF THE DRAWINGS

FIG. 2 is a diagram schematically illustrating multiple wires in a catheter braid used for signal transmission, in accordance with an embodiment of the present invention; and FIG. 3 is a flow chart that schematically illustrates a method for interference-proof magnetic position tracking, in accordance with an embodiment of the present invention.

DETAILED DESCRIPTION OF EMBODIMENTS

Overview

Figure 1:
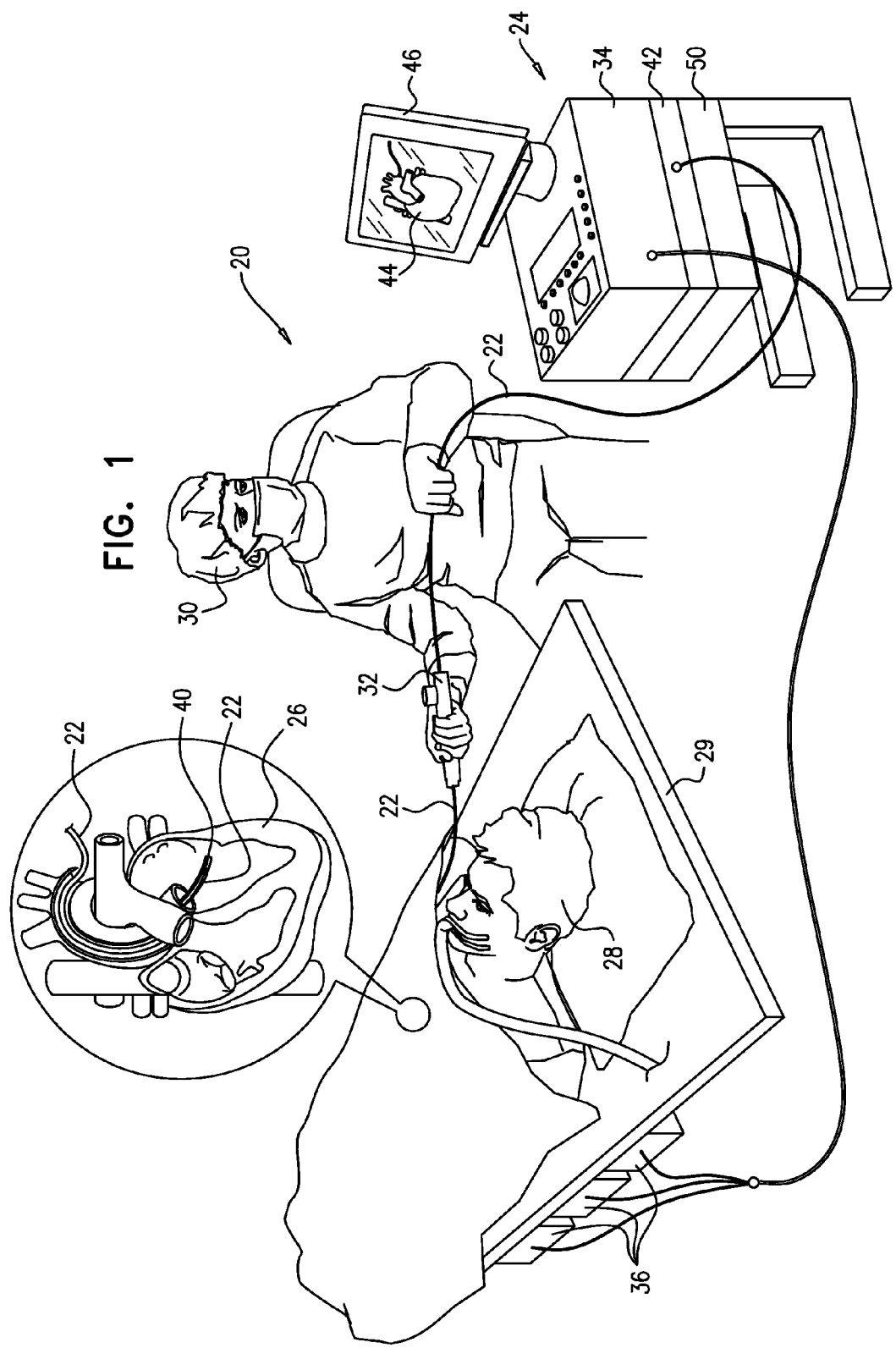
FIG. 1 is a schematic, pictorial illustration of a catheter tracking system, in accordance with an embodiment of the present invention.

Catheters are used in a variety of therapeutic and diagnostic medical procedures. A catheter is percutaneously inserted into the cardio-vascular system of a living body, typically a medical patient. The catheter distal end is navigated to a target region in an organ of the body, typically a heart cavity, to perform the medical procedure.

The catheter may tracked in the living body by techniques such as magnetic position sensing. When using magnetic position sensing, a magnetic field sensor is installed near the distal end of the catheter. Magnetic fields, which are generated externally to the body by a catheter position tracking system, induce electrical signals in the distal-end sensor. The induced electrical signals are used by a processor in the system to compute the position of the magnetic sensor, thus tracking the distal end of the catheter in the body. The electrical signals are typically transferred from the distal-end sensor to the processor using electrical wires traversing the catheter.

Embodiments of the present invention that are described herein provide improved methods and systems for transferring electrical signals through intra-body probes such as catheters. In some embodiments, the catheter comprises a braid of electrical wires for providing flexibility, structural strength and kink resistance. Two of the braid wires are used for transferring the electrical signals sensed by the distal-end sensor along the catheter en-route to the external processor.

In some embodiments, a dummy load is fitted adjacent to the distal-end sensor, and an additional pair of braid wires is used for transferring signals induced in the dummy load. The dummy load may comprise a resistor, or may be formed by electrically connecting both wires in the pair. By subtracting the signals received over the two pairs of wires, it is possible to cancel noise and interference, e.g., inductive pickup in the wires, which may distort the position measurements.

The disclosed techniques are not limited to position sensors fitted in the distal end. For example, braid wires can be used for transferring ablation current to ablation electrodes, and/or for transferring signals measured by electrophysiological (EP) mapping electrodes. Such electrodes may be mounted near the distal end or at any other suitable location along the catheter. EP mapping signals can also be protected from interference using a dummy-load mechanism.

The methods and systems described herein are highly effective in canceling noise and interference in the signals sensed by the catheter sensors, and therefore enable accurate position sensing and EP mapping even in harsh electromagnetic environments. Since the disclosed techniques re-use the existing braid wires for signal transmission, they eliminate the need for additional cabling that traverse the catheter lumen, as well as for additional shielding. This saving in volume can be used for vacating the catheter lumen for other purposes, or for reducing the catheter diameter.

System Description

FIG. 1 is a schematic, pictorial illustration of a catheter tracking system 20, in accordance with an embodiment of the present invention. System 20 comprises a probe 22, in the present example a cardiac catheter, and a control console 24. In the embodiment described herein, catheter 22 may be used for any suitable therapeutic and/or diagnostic purposes, such as ablation of tissue in a heart 26 and the mapping of electro-cardiac signals for the diagnosis of cardiac dysfunctions, such as cardiac arrhythmias, for example.

Console 24 comprises a processor 42, typically a general-purpose computer, with suitable front end and interface circuits for receiving signals from catheter 22 (such as differential signals as will be described later) and for controlling the other components of system 20 described herein. Processor 42 may be programmed in software to carry out the functions that are used by the system, and the processor stores data for the software in a memory 50. The software may be downloaded to console 24 in electronic form, over a network, for example, or it may be provided on non-transitory tangible media, such as optical, magnetic or electronic memory media. Alternatively, some or all of the functions of processor 42 may be carried out by dedicated or programmable digital hardware components.

An operator 30, typically a physician, inserts catheter 22 through the vascular system of a patient 28 lying on a table 29. Operator 30 moves a distal end 40 of catheter 22 in the vicinity of the target region in heart 26 by manipulating catheter 22 with a manipulator 32 near the proximal end of the catheter as shown in the inset of FIG. 1. The proximal end of catheter 22 is connected to interface circuitry in processor 42.

The position of the distal end of the probe in the heart cavity is typically measured by magnetic position sensing in catheter tracking system 20. In this case, console 24 comprises a driver circuit 34, which drives magnetic field generators 36 placed at known positions external to patient 28 lying on table 29, e.g., below the patient's torso.

A magnetic field sensor is installed in catheter 22 near distal end 40 (not shown in FIG. 1, but will be shown in FIG. 2 below). The sensor generates electrical position signals in response to the magnetic fields from the coils, thereby enabling processor 42 to determine the position, (e.g., the location and orientation) of catheter distal end 40 within the heart cavity. Cabling within the lumen of catheter 22 connect the magnetic sensor at catheter distal end 40 to interface circuitry in processor 42 at the catheter proximal end. Operator 30 can view the position of catheter distal end 40 on an image 44 of heart 26 on a user display 46.

This method of position sensing is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Re-Using Catheter Braid Wires for Signal Transmission

In some embodiments, to enhance mechanical flexibility and kink resistance when guided through the patient's cardiovascular system, a catheter braid may be disposed along the length of the catheter from the proximal to distal end. The catheter braid is typically formed from multiple wires which are woven into the desired braid configuration. The braid may be placed in any suitable position within the catheter lumen along the length of the catheter. For the embodiments to be shown later herein, the multiple wires are typically coiled along the length of the elongate member to form the catheter braid.

The catheter braid wire may be woven into a mesh, spiral coil, or any suitable pattern. In the context of the present patent application and in the claims, the terms "braid" and "braid wires" refer to any suitable configuration of the wires, including various meshed and coiled configurations.

In the embodiments of the present invention, pairs of wires chosen from among the multiple wires forming the catheter braid are used to form electrical interconnects to relay signals between elements near the catheter's distal end to medical equipment at the proximal end.

FIG. 2 is a diagram schematically illustrating multiple wires 103 in a catheter braid 100 used for signal transmission, in accordance with an embodiment of the present invention. In the upper portion of FIG. 2, operator manipulator 32 is connected to catheter 22 at the catheter proximal end. Catheter braid 100 is formed from multiple catheter braid wires 103, typically metal wires, and are shown in the upper portion of FIG. 2 as a metal coil braid.

Catheter 22 comprises an insertion tube 105 and multiple wires 103 that are coiled around the length of an elongate flexible member 110. Elongate flexible member 110 is configured to be inserted into insertion tube 105. Two pairs of wires can be seen in FIG. 2. A first wire pair 130 (shown as bold lines) is connected to a single-axis magnetic sensor 115 at distal end 40, and a second wire pair 125 (shown as dotted lines) is connected to a dummy load 120 that is adjacent to sensor 115. Dummy load 120 may comprise any suitable combination of resistors, inductors, capacitors, a short, or any suitable electronic element for terminating second wire pair 125.

Braid 100 is shown as if there are two pairs connected across sensor 115 and dummy load 120, e.g., four wires that coil around elongate member 110 to form braid 100. However, braid 100 may be formed from any suitable number of wires. Any suitable number of wire pairs may be chosen from among the multiple wires in braid 100 to connect to any number of elements at catheter distal end 40 to medical equipment at the catheter proximal end. Typically, the braid wires used for signal transmission are electrically-insulated from one another and from other braid wires.

The catheter structure shown in FIG. 2 is for conceptual clarity and not by way of limitation of the embodiments of the present invention. There are many catheter structures and configurations which can be used depending in the medical procedure as described previously. For example, although FIG. 2 shows a braid in which the wires are coiled, i.e., wound helically, in alternative embodiments the wires may be braided in any other suitable way, such as in a cross-braiding configuration.

Moreover, the disclosed techniques can be used with various other kinds of probes. In some embodiments, the probe comprises a guide-wire fitted with a magnetic sensor similar to sensor 115 (e.g., a single-axis sensor) and a dummy load similar to dummy load 120.

In some embodiments, catheter 22 comprises an insertion tube 105. Braid 100 is coiled around elongate member 110, the elongate member inserted into any suitable position within the lumen of insertion tube 105 and contained in the insertion tube. In some embodiments, the elongate member may be potted and held rigidly within the insertion tube.

In other embodiments, the catheter may comprise a multilayered insertion tube formed from an outer layer, the braid, and an inner layer forming the inner wall of the catheter lumen. In terms of the embodiment shown in FIG. 2, elongate member 110 comprises a second flexible tube. The second flexible tube is contained within insertion tube 105 and connected to the insertion tube along the length of the insertion tube, thus forming the inner wall of the catheter lumen. Braid 100 is sandwiched between insertion tube 102 and the second flexible tube.

The insertion tube and elongate flexible member are typically formed from polymers, but may be formed from any suitable material by any suitable method, such as extrusion. Similarly, any type of braid pattern of multiple wires 103 may be implemented, such that braid 100 is not limited to a coil as shown in FIG. 2. Wires 103 may be formed from metal or any suitable conducting material to provide mechanical flexibility to the catheter. The multiple wires may be insulated. The sensor and/or any suitable elements may be connected to the wire through openings formed in the insulation. The magnetic sensor at distal end 40 is not limited to a single-axis sensor, but may be any suitable sensor structure.

Noise Reduction in Catheter Braid Wire Interconnects

When catheter 22 is placed in the patient's body, the wires that traverse the length of the catheter from connecting electrodes and/or sensors near the distal end to medical equipment at the proximal end are subject to various spurious noise sources. For example, the induced differential electrical signal from sensor 115 in response to the magnetic field generated by magnetic sources 36 may be corrupted by different noise sources as the differential signal traverses pair 130 in braid 100. Particularly, inductive pickup from magnetic sources 36 in the unshielded pair 130 can give rise to spurious signals from magnetic sources 36. Inductive pickup can also come from an RF generator (e.g., driver circuit 34 that drives field generators 36).

In some embodiments, dummy load 120 is placed next to sensor 115. Second pair 125 of wires is connected across dummy load 120. The two wire pairs (130 and 125) experience approximately the same noise environment along the length of catheter 22 from the distal to the proximal end of catheter 22. As a result, any spurious noise pickup induced in second pair 125 with dummy load 120 can be used to remove the spurious noise pickup in the differential signal in the first pair 130, which corrupts the signal from single-axis sensor 115.

In some embodiments, differential amplifier circuitry 135 can be used to measure and amplify the respective signals from sensor 115 and dummy load 120 from first pair 130 and second pair 125, respectively, by any suitable method. In the present example, a first differential amplifier 140 amplifies the differential signal from sensor 115 in first pair 130. The single ended signal output of amplifier 140 is denoted S.

Similarly, a second differential amplifier 145 amplifies the signal from dummy load 120 in second pair 125. The single ended signal output of amplifier 145 is denoted N for the spurious (common-mode) inductive pickup noise coupled into the wires of second pair 125. Differential amplifier circuitry 135 may be a separate unit, or it may be integrated within processor unit 42 at the proximal end of catheter 22.

As mentioned previously, signal S is the sensor signal corrupted by spurious pickup noise. Processor 42 is configured to use the noise N to remove the noise from the sensor signal. In some embodiments, processor 42 may use the noise N in second pair 125 to remove the noise N from the sensor signal S transmitted along the length of first pair 130 by any suitable digital and/or analog technique, such as subtracting the noise N from the signal S. Alternatively, analog subtraction of N from S can be performed internally in circuitry 135. In either case, processor 42 estimates the position coordinates of sensor 115 (and thus of distal end 40) based on the interference-free signal S-N.

FIG. 3 is a flow chart that schematically illustrates a method for interference-proof catheter position tracking, in accordance with an embodiment of the present invention. In an inserting step 200, catheter 22 is inserted into patient body 28 with magnetic sensor 115 and dummy load 120 near catheter distal end 40. In an applying step 210, a magnetic field is applied to patient body 28 from magnetic sources 36. In a first measuring step 220, circuitry 135 measures the induced signal S across first wire pair 130 connected across sensor 115 near catheter distal end 40. In a second measuring step 230, circuitry 135 measures the signal N across second pair 125 connected across dummy load 120 near catheter distal end 40.

In a computing step 240, processor 42 computes signal S-N to remove unwanted noise N from the original signal S induced in distal end sensor 115 in response to the applied magnetic field. In a position calculation step 250, processor 42 uses computed signal S-N to calculate the position of catheter distal end 40 in patient body 28.

The term "external subsystem" refers to any suitable combination of processor 42, differential amplifier circuitry 135, or any other medical equipment circuitry needed to perform the functions of catheter tracking system 20 described herein in accordance with the embodiments of the present invention.

Although the embodiments described herein mainly address cardiac catheters, the methods and systems described herein can also be used in other applications, such as in catheters or location-enabled guide-wires used in other body organs and in other types of intra-body probes.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A probe, comprising:
   an insertion tube;
   a magnetic field sensor;
   a dummy load mounted adjacent to the magnetic field sensor;
   a braid comprising multiple braid wires that traverse a length of the insertion tube, herein a first pair of the braid wires is connected across the magnetic field sensor, and a second pair of the braid wires is connected across the dummy load; and
   circuitry that is configured to cancel interference in a first signal transferred over the first pair of the braid wires using a second signal transferred over the second pair of braid wires.

2. The probe according to claim 1, wherein the magnetic field sensor comprises a single-axis sensor.

3. The probe according to claim 1, wherein the probe comprises a cardiac catheter.

4. The probe according to claim 1, wherein the probe comprises a cardiac guide-wire.

5. The probe according to claim 1, and comprising an elongate flexible member that is contained within the insertion tube, such that the braid is located between the insertion tube and the elongate flexible member.

6. The probe according to claim 1, wherein each of the braid wires in the first pair and the second pair is electrically-insulated from the other braid wires.

7. The probe according to claim 1, wherein the circuitry is configured to subtract the second signal from the first signal.

8. A method for fabricating a probe, the method comprising:
   mounting a magnetic field sensor and a dummy load adjacent to one another in an insertion tube;
   adjacent to one another in an insertion tube;
   placing along the insertion tube a braid comprising multiple braid wire so as to traverse a length of the insertion tube;
   connecting a first pair of the braid wires across the magnetic field sensor, and connecting a second pair of the braid wires across the dummy load; and
   providing circuitry that cancels interference in a first signal transferred over the first pair of braid wires using a second signal transferred over the second pair of braid wires.

9. The method according to claim 8, wherein the magnetic sensor comprises a single-axis sensor.

10. The method according to claim 8, wherein the probe comprises a cardiac catheter.

11. The method according to claim 8, wherein the probe comprises a cardiac guide-wire.

12. The method according to claim 8, and comprising placing an elongate flexible member within the insertion tube, such that the braid is located between the insertion tube and the elongate flexible member.

13. The method according to claim 8, wherein each of the braid wires in the first pair and the second pair is electrically-insulated from the other braid wires.

14. The method according to claim 8, wherein the first circuitry subtracts the second signal from the first signal.

15. A method for position tracking, comprising:
    inserting into a living body a probe, which comprises an insertion tube, a magnetic field sensor, a dummy load mounted adjacent to the magnetic field sensor, and a braid comprising multiple braid wires that traverse a length of the insertion tube, wherein a first pair of the braid wires is connected across the magnetic field sensor, and a second pair of the braid wires is connected across the dummy load;
    applying a magnetic field to the living body;
    measuring a first signal across the first pair;
    measuring a second signal across the second pair;
    applying the second signal to the first signal so as to remove interference from the first signal; and
    computing a position of the magnetic field sensor in the living body from the first signal after removing the interference.

16. The method according to claim 15, wherein applying the second signal to the first signal comprises subtracting the second signal from the first signal.

17. A position tracking system, comprising:
    a probe, which is inserted into a living body and comprises an insertion tube, a magnetic field sensor, a dummy load mounted adjacent to the magnetic field sensor, and a braid comprising multiple braid wires that traverse a length of the insertion tube, wherein a first pair of 30 the braid wires is connected across the magnetic field, and a second pair of the braid wires is connected across the dummy load; and
    an external subsystem, which is configured to apply a magnetic field to the living body, to measure a first signal across the first pair, to measure a second signal across the second pair, to apply the second signal to the first signal so as to remove interference from the first signal, and to compute a position of the magnetic field sensor in the living body from the first signal after removing the interference.

18. The position tracking system according to claim 17, wherein the external subsystem is configured to apply the second signal to the first signal by subtracting the second signal from the first signal.

* * * * *